United States Patent
Salek et al.

Patent Number: 5,336,812
Date of Patent: Aug. 9, 1994

[54] METHOD OF MAKING 1,1-BIS-(4-HYDROXYPHENYL)-3,3,5-TRIMETHYLCYCLOHEXANE

[75] Inventors: Jeffrey S. Salek, Oakdale Borough; Joseph Pugach, Monroeville Borough; Mark R. Rubino, Municipality of Monroeville, all of Pa.

[73] Assignee: Aristech Chemical Corporation, Pittsburgh, Pa.

[21] Appl. No.: 150,893

[22] Filed: Nov. 12, 1993

[51] Int. Cl.$^5$ ............ C07C 37/20; C07C 39/15; C07C 39/17
[52] U.S. Cl. ............ 568/721; 508/69
[58] Field of Search ............ 568/721, 724

[56] References Cited

U.S. PATENT DOCUMENTS

| | | | |
|---|---|---|---|
| 2,730,552 | 1/1956 | Williamson | 568/721 |
| 2,791,616 | 5/1957 | Luten | 568/724 |
| 3,491,157 | 1/1970 | Dietzler et al. | 568/721 |
| 4,942,265 | 7/1990 | Imuro et al. | 568/724 |
| 4,964,890 | 10/1990 | Reuter et al. | 55/158 |
| 4,982,014 | 1/1991 | Freitag et al. | 568/721 |
| 5,210,328 | 5/1993 | Freitag et al. | 568/721 |
| 5,276,213 | 1/1994 | Serini et al. | 568/721 |

Primary Examiner—Joseph E. Evans
Attorney, Agent, or Firm—William L. Krayer

[57] ABSTRACT

A process for making 1,1-bis-(4-hydroxyphenyl)-3,3,5-trimethylcyclohexane via the acid catalyzed reaction of phenol and 3,3,5-trimethylcyclohexanone containing an organic thiol co-catalyst is described wherein the organic thiol is rejuvenated by treatment with a halogen acid and recycled to a fresh mixture of phenol and 3,3,5-trimethylcyclohexanone to make additional 1,1-bis-(4-hydroxyphenyl)-3,3,5-trimethylcyclohexane.

11 Claims, No Drawings

METHOD OF MAKING 1,1-BIS-(4-HYDROXYPHENYL)-3,3,5-TRIMETHYLCYCLOHEXANE

TECHNICAL FIELD

This invention relates to the manufacture of 1,1-bis-(4-hydroxyphenyl)-3,3,5-trimethylcyclohexane and particularly to an improvement comprising recovering and rejuvenating the alkane thiol co-catalyst from a complex reaction mixture. The alkane thiol co-catalyst may be recycled or used in a sequential reactor for the initial reactants, phenol and 3,3,5-trimethylcyclohexanone.

BACKGROUND OF THE INVENTION

In U.S. Pat. Nos. 4,964,890, 4,982,014, and 5,210,328, which are incorporated herein by reference, Freitag et al describe the manufacture of 1,1-bis-(4-hydroxyphenyl)-3,3,5-trimethylcyclohexane (hereinafter called "Bisphenol TMC" or "BPTMC") by the reaction of 3,3,5-trimethylcyclohexanone ("TMC" or dihydroisophorone) with phenol in the presence of an acid condensation catalyst and an organic sulfur compound as a co-catalyst, preferably an alkane thiol. However, no method of saving or recycling the co-catalyst is disclosed, either for the sake of economy or for environmental reasons.

SUMMARY OF THE INVENTION

We have invented a method of recovering and reusing alkane thiol co-catalysts from the reaction mixture for the manufacture of Bisphenol TMC.

As typified in U.S. Pat. No. 4,982,014, Bisphenol TMC can be made by the reaction of phenol and TMC in the presence of an acid catalyst and an alkane thiol co-catalyst. The alkane thiol co-catalyst may have the formula $R^1R^2CHSH$ where $R^1$ is an alkyl, aryl or alkaryl group having 1 to about 20 carbon atoms and $R^2$ is H or $R^1$. The desired Bisphenol TMC product is filtered from the reaction mixture as a solid, leaving a mixture of organic and inorganic materials which the prior art literature has not addressed, to our knowledge.

We have found that the alkane thiol co-catalysts used in the reaction can be recovered and rejuvenated in a simple fashion. At the completion of the reaction, water is added to the reaction mixture to form a slurry. Filtration of this slurry results in the recovery of a filter cake consisting of an adduct of BPTMC and phenol. This solid adduct is further treated to obtain high purity BPTMC product. Treatments to remove phenol and enhance purity include aqueous and/or organic triturations, steam stripping, and/or thermal "cracking" under vacuum. We have also found that treatment of the reaction mixture with caustic is not necessary to obtain high quality and good yield.

The filtrate separates into an aqueous and organic phase. The organic phase consists of unreacted starting materials, alkane thiol and intermediate reaction products. A fraction of the thiol exists as a dithioketal of TMC which has little or no activity as a catalyst for the reaction. A further portion of the thiol exists in the form of vinylic thiol ethers of TMC. It is a purpose of this invention to convert the dithioketal to species with enhanced catalytic activity.

We have found that by simple treatment of the organic phase with HCl and heat, the dithioketal is converted into alkane thiol and vinylic thiol ethers. This is surprising in view of the fact that dithioketals are not readily destroyed by simple treatment with HCl. More complicated methods are used to destroy them, the most common of which is treatment with mercuric oxide or a mercuric salt.

Furthermore, unconverted starting materials and intermediates are converted to BPTMC which is ultimately recovered, and improves the overall yield of the reaction. This is also surprising, because heating the original reaction mixture decreases reaction efficiency.

The HCl treated organic phase is then recycled back to a reaction zone, additional phenol and TMC are added, and the reaction started. It is found that the results obtained are similar to those using virgin alkane thiol. It appears that the repetition of the above-described procedure can continue in this manner.

Our invention is thus an improvement in the manufacture of Bisphenol TMC from phenol and TMC, wherein Bisphenol TMC after treatment with water is separated from the reaction mixture by filtration to obtain (1) a solid including Bisphenol TMC, (2) an aqueous filtrate, and (3) an organic filtrate, which improvement comprises adding an acid such as hydrochloric acid, to said organic filtrate, and heating at a temperature from about 0° C. to about 150° C. to make additional Bisphenol TMC which may be separated by filtration. The remaining organic filtrate may then be recycled to the original reaction; alternatively, the organic filtrate so treated may be reused for its catalyst content without filtering out the BPTMC.

DETAILED DESCRIPTION OF THE INVENTION

Our invention is applicable to any procedure for the manufacture of Bisphenol TMC from one mole of TMC and two moles of phenol using an acid catalyst with an alkane thiol co-catalyst as described above. The examples of U.S. Pat. No. 4,982,014 (the entirety of which is incorporated by reference) use dodecylthiol and butanethiol as co-catalysts. We may use these co-catalysts and any other within the formula given above, specifically $R^1R^2CHSH$ where $R^1$ is an alkyl, aryl or alkaryl group having 1 to about 20 carbon atoms and $R^2$ is H or $R^1$, in the methods and processes taught in the '014 patent.

EXAMPLE 1

In this example, 14.9 g (106.3 mmol) of TMC and 60 g (637.6 mmol) of phenol were reacted in the presence of 0.78 g (5.3 mmol) of octane thiol for six hours while feeding HCl at the rate of 1.2 mmol/minute. 100 g of deionized water was added and the resulting slurry was suction filtered. The resulting filter cake consisting of 1:1 adduct of BPTMC and phenol was triturated twice with hot water giving 21.0 g of slightly yellow Bisphenol TMC, (67.7 mmol), 97.9% purity, 14 ppm phenol.

The filtrate separated into an aqueous and an organic phase. The dark organic phase was removed by pipette as a liquid (17.5 g), and was treated with HCl (0.6 mmol/min.), heated and analyzed at the times indicated in Table I.

TABLE 1

| Time | Area Percent - Gas Chromatograph | | | | | | | |
|---|---|---|---|---|---|---|---|---|
| | CpdsA | TMC | phenol | CpdB | RSH | Int's | DTK | BPTMC |
| Initial (rm temp) | 0.030 | 10.98 | 74.84 | 0.54 | 0.60 | 7.38 | 0.45 | 3.98 |
| 2 hrs (rt → 60°) | 0.050 | 9.29 | 70.63 | 0.55 | 0.63 | 7.16 | 0.37 | 5.20 |
| 4.75 hrs (60 → 75°) | 0.23 | 5.63 | 70.42 | 0.57 | 1.29 | 10.18 | 0.06 | 7.80 |
| 22 hrs (75° → rt) | 0.29 | 0.02 | 67.76 | 0.43 | 2.09 | 5.40 | 0.19 | 23.20 |

CpdsA means unknown compounds with retention times less than 8.3 minutes; RSH is the alkane thiol, in this case the octane thiol; Int's means intermediates, which includes vinylic thiol ethers, and DTK is dithioketal.
CpdB means a compound having a retention time of 10.9 minutes.

The results in Table I demonstrate that catalytically active sulfur species are produced with the concomitant destruction of the dithioketal. It is also shown that additional BPTMC is formed from the phenol and TMC present in the organic phase.

After 22 hours, the HCl treated organic phase containing the rejuvenated thiol catalyst was mixed with 13.4 g of TMC (95.6 mmol) and 54.0 g of phenol (573.4 mmol), and the reaction was conducted again at room temperature for a period of 21 hours while HCl was delivered at a rate of 0.4 mmol/min. The reaction mixture was treated as before with 100 g of deionized water, and the resultant BPTMC/phenol adduct was triturated with toluene. This gave 26.3 g of a fluffy white solid (84.7 mmol), 99.7% purity, 10 ppm phenol.

The organic phase (5.1 g) from the filtrate was treated for 24 hours with HCl as before, with the results indicated in Table IA.

TABLE IA

| RX Time | Area % - Gas Chromatograph | | | | | | | |
|---|---|---|---|---|---|---|---|---|
| | CpdsA | TMC | Phenol | CpdB | RSH | Int's | DTK | BPTMC |
| Initial | 0.43 | 7.85 | 71.22 | 0.65 | 0.66 | 7.34 | 0.70 | 4.49 |
| 2 hrs | 0.41 | 6.10 | 64.66 | 0.75 | 0.91 | 12.98 | 0.17 | 8.20 |
| 4.75 hrs | 0.62 | 3.13 | 64.00 | 0.71 | 0.81 | 11.97 | 0.26 | 13.13 |
| 24 hrs | 0.33 | 0.11 | 66.00 | 0.65 | 1.36 | 10.22 | 0 | 17.63 |

CpdsA and CpdB are the same as in Table I.

The HCl-treated organic phase obtained from this was again blended with additional TMC and phenol—9.4 g (67.0 mmol) and 37.9 g (402.7 mmol), respectively. The reaction was again conducted at room temperature, for 21 hours, delivering HCl at 0.4 mmol/min. 15.1 g of fluffy white solid was obtained (48.6 mmol), 99.6% purity, 15 ppm phenol.

Table IB summarizes the results.

TABLE IB

| Run | BPTMC mmol | Phenol, ppm | Purity | Comments |
|---|---|---|---|---|
| Initial | 67.7 | 14 | 97.9% | |
| 1st recycle | 84.7 | 10 | 99.7% | toluene trituration* |
| 2nd recycle | 48.6 | 15 | 99.6% | toluene trituration* |
| Total | 201.0 mmol** | | | |

*for separating the BPTMC/phenol adduct
**75% over 3 runs, based on TMC

It appears that the reuse of the co-catalyst may continue in this manner.

EXAMPLE 2

In this experiment, the initial run was repeated as in Example 1 except that the HCl delivery rate was reduced from about 1.2 mmol/min to about 0.4 mmol/min. 17.5 g of pale yellow (BPTMC) powder was recovered (56.4 mmol) at 97.9% purity; 66 ppm phenol. The organic phase was extracted with 13.4 g TMC (95.6 mmol) giving 47.2 g of a dark green liquid which was treated with HCl and heated as in Example 1. The reaction was recommenced after the addition of 54.0 g (573.8 mmol) of phenol. 39.1 g of faintly yellow powder (126.0 mmol) was obtained by filtration at 97.4% purity; 87 ppm phenol.

These results are summarized in Table II.

TABLE II

| Experiment | BPTMC mmol | Purity | phenol, ppm | Comments |
|---|---|---|---|---|
| Initial Run | 56.4 | 97.9% | 66 | H₂O trituration* |
| First recycle Run | 126.0 | 97.4% | 87 | H₂O trituration* |
| Total | 182.4 mmol** | | | |

*for separating the BPTMC/phenol adduct
**90% over 2 runs, based on TMC

EXAMPLE 3

The initial reaction was repeated as in Example 2; 22.3 g of a pale yellow powder was obtained: 71.8 mmol, 98.6% purity; 22 ppm phenol.

The organic phase of the filtrate was "extracted" with 25 ml of diethyl ether, and treated with HCl—about 0.4 mmol/min for 5 hours at room temperature, followed by a 16 hour sparge with Argon to remove the ether. Then 13.4 g TMC (95.6 mmol) TMC and 54 g phenol (573.8 mmol) phenol were added and the reaction was recommenced, running for 5.5 hours. 28.5 g of pale yellow powder (91.8 mmol), 98.6% purity, 23 ppm phenol were recovered, as shown in Table III.

TABLE III

| Experiment | BPTMC mmol | Purity | Phenol, ppm | Comments |
|---|---|---|---|---|
| Initial Run | 71.8 | 98.6% | 22 | H₂O trituration* |
| 1st recycle | 91.8 | 97.6% | 23 | H₂O trituration* |

TABLE III-continued

| Experiment | BPTMC mmol | Purity | Phenol, ppm | Comments |
|---|---|---|---|---|
| Total | 163.6 mmol** | | | |

*for separating the BPTMC/phenol adduct
**79% over 2 runs, based on TMC

EXAMPLE 4 COMPARATIVE

Three runs were made according to the conditions of Example 1 in order to compare the use of virgin alkane thiol, acid-treated co-catalyst according to the invention, and untreated co-catalyst. The first run in Table IV used virgin alkane thiol. The second run used the organic layer following the rejuvenation process. The third run used untreated organic layer.

The results displayed in Table IV were determined through gas chromatographic analysis of reaction aliquots which were first silylated using N,O-bis(trimethylsilyl)acetamide. The Ratio heading represents the area % sum of starting materials (TMC and silylated phenol) divided by the area % of product (silylated BPTMC). At 100% TMC conversion, this ratio will decrease to about 1.8. The higher the ratio, the less reaction has occurred. The data show that after 6 hours of reaction, virgin alkane thiol and "rejuvenated" organic phase displayed comparable effectiveness while untreated organic phase had significantly less activity.

TABLE IV

| Experiment | Ratio* |
|---|---|
| Control (virgin alkane thiol) (0.10 equiv. alkane thiol) | 3.0 |
| Acid-Treated Organic Phase (0.05 equiv. alkane thiol initially) | 1.9 |
| Untreated Organic Phase (0.10 equiv. alkane thiol initially) | 36.5 |

*Represents the gas chromatogram area % sum of starting materials (TMC and silylated phenol) divided by the area % of product (silylated BPTMC).

We claim:

1. In a method of making 1,1-bis-(4-hydroxyphenyl)-3,3,5-trimethylcyclohexane in the form of an adduct with phenol wherein 3,3,5-trimethylcyclohexanone is reacted with phenol in the presence of an acid condensation catalyst and an alkane thiol of the formula $R^1R^2CHSH$ where $R^1$ is an alkyl, aryl or alkaryl group having from 1 to about 20 carbon atoms and $R^2$ is H or $R^1$, to obtain a reaction mixture including 1,1-bis-(4-hydroxyphenyl)-3,3,5-trimethylcyclohexane in the form of an adduct with phenol, the improvement comprising adding water to said reaction mixture to obtain a slurry, filtering said slurry to obtain 1,1-bis-(4-hydroxyphenyl)-3,3,5-trimethylcyclohexane phenol adduct as a solid, and a filtrate having an organic phase and an aqueous phase, recovering said organic phase, contacting said organic phase with an acid condensation catalyst at a temperature of about 0° C. to about 150° C., and adding phenol and 3,3,5-trimethylcyclohexanone to the organic phase so treated to make additional 1,1-bis-(4-hydroxyphenyl)-3,3,5-trimethylcyclohexane.

2. Method of claim 1 wherein the acid condensation catalyst is hydrochloric acid.

3. Method of claim 1 wherein the molar ratio of phenol to 3,3,5-trimethylcyclohexanone in the original reaction mixture is about 2:1 to about 15:1.

4. Method of claim 1 wherein phenol is separated from the adduct to obtain 1,1-bis-(4-hydroxyphenyl)-3,3,5-trimethylcyclohexane.

5. Method of claim 4 wherein the separation is accomplished by trituration with an organic solvent.

6. Method of making 1,1-bis-(4-hydroxyphenyl)-3,3,5-trimethylcyclohexane comprising (a) reacting 3,3,5-trimethylcyclohexanone with phenol in the presence of an acid condensation catalyst and a thiol co-catalyst of the formula $R^1R^2CHSH$ where $R^1$ is an alkyl, aryl, or alkaryl group having from 1 to about 20 carbon atoms and $R^2$ is H or $R^1$ to obtain a reaction mixture including 1,1-bis-(4-hydroxyphenyl)-3,3,5-trimethylcyclohexane in the form of an adduct with phenol, (b) adding water to said reaction mixture to obtain a slurry, (c) filtering said slurry to obtain said adduct in the form of a solid and also to obtain an organic filtrate and an aqueous filtrate, (d) treating said adduct to separate phenol from said 1,1-bis-(4-hydroxyphenyl)-3,3,5-trimethylcyclohexane/phenol adduct, thereby recovering said 1,1-bis-(4-hydroxyphenyl)-3,3,5-trimethylcyclohexane, (e) recovering said organic filtrate, adding an acid condensation catalyst to said organic filtrate and heating said organic filtrate to reactivate said thiol co-catalyst, (f) adding fresh phenol and 3,3,5-trimethylcyclohexanone to said organic filtrate to make more of said adduct, and repeating steps (b), (c) and (d).

7. Method of claim 6 followed by repetition of step (e).

8. Method of claim 7 followed by repetition of step (f).

9. Method of claim 6 wherein the acid condensation catalyst is hydrochloric acid.

10. Method of claim 6 wherein the ratio of phenol to 3,3,5-trimethylcyclohexanone in step (a) is about 2:1 to about 15:1.

11. Method of claim 6 wherein the ratio of phenol to 3,3,5-trimethylcyclohexanone in step (f) is about 2:1 to about 15:1.

* * * * *